United States Patent [19]

Balaraman et al.

[11] Patent Number: 5,656,459
[45] Date of Patent: Aug. 12, 1997

[54] PROCESS FOR THE PREPARATION OF CYCLOSPORIN A FROM TOLYPOCLADIUM SPECIES

[76] Inventors: Kothandapani Balaraman, No. 10, Second Cross Tagorenagar, Pondieling 605008, India; Nisha Mathew, No. 122, Muthiamuda liar Street, Muthial pet, Pondicherry-3, India

[21] Appl. No.: 491,566

[22] Filed: Jun. 16, 1995

[51] Int. Cl.$^6$ .............. C12P 21/04; C12P 21/00; C12N 1/14

[52] U.S. Cl. ............ 435/71.3; 435/71.1; 435/254.1; 435/911

[58] Field of Search .................. 435/71.1, 71.3, 435/254.1, 911

[56] References Cited

U.S. PATENT DOCUMENTS 4,289,851 9/1981 Traber et al. .................. 435/71.1
5,256,547 10/1993 Andat et al. .................. 435/71.1
5,382,655 1/1995 Seanya et al. .................. 530/317
5,447,854 9/1995 Goto et al. .................. 435/71.3

*Primary Examiner*—Herbert J. Lilling
*Attorney, Agent, or Firm*—Spencer & Frank

[57] ABSTRACT

The invention relates to a process for the preparation of cyclosporin A from Tolypocladium Sp comprising in the step of preparing a fermented medium of said Tolypocladium sp. The fungal biomass is extracted of said fermented medium to obtain a methanol extract, which methanol is removed by evaporation to obtain a first residue. An ethyl acetate extract is prepared from the aqueous solution of said first residue, which is decolourized and concentrated to obtain a second residue, the second residue is subjected to a step of purification.

18 Claims, 3 Drawing Sheets

PROCESS FOR THE PREPARATION OF CYCLOSPORIN A FROM TOLYPOCLADIUM SPECIES

FIELD OF THE INVENTION

This invention relates to a process for the preparation of cyclosporin A from Tolypocladium species as herein described.

DESCRIPTION OF RELATED ART

It is generally known that cyclosporin A has a useful application as an immuno suppressive agent for the prevention of organ rejection in transplantation surgery. By the known process, cyclosporin is prepared as a complex by the cultivation of the strain of *Tolypocladium varium* fungus species. Thus, British Patent no. 2227489 discloses a microbial process for the production of a cyclosporin complex or its components viz, cyclosporin A, cyclosporin B and cyclosporin C. Such a known process suggests cultivating a strain of *Tolypocladium varium* fungus species to produce the cyclosporin complex on a nutrient medium. The nutrient medium comprises carbon sources, organic and inorganic nitrogen sources and mineral salts, as are normally used in fermentation broths. The fermentation is carried out as usual under aerobic conditions at 25° to 30° C. The cyclosporin complex produced, is if desired, isolated and purified to produce a purified complex.

The known art process suggests a preferred fermentation medium which contains peptone, ammonium sulphate and tryptone as nitrogen source. The preferred carbon sources are glucose, maltose and sorbitol. The culture *Tolypocladium varium* sp nov. Cy/93 is deposited as NCAIM (P) F-001005. The known processes do not suggest a process of producing only cyclosporin A and of a high purity of not less than 98%.

OBJECTS OF THE INVENTION

An object of this invention is to propose an improved process for the preparation of cyclosporin A.

Another object of this invention is to propose a process for the preparation of cyclosporin A having a high yield.

Yet another object of this invention is to propose a process for the preparation of cyclosporin A of substantially uniform purity.

DESCRIPTION OF THE INVENTION

The present invention employs a novel fungus Tolypocladium sp. and deposited under NRRL No. 18950. The characteristics of other species of Tolypocladium with reference to the species of the present invention are shown in Table 1.

TABLE 1

Comparison of characteristics of different species of Tolypocladium

| Characters | T. inflatum | T. Cylindrosporum | T. geodus | Tolypocladium Sp. |
| --- | --- | --- | --- | --- |
| Growth | slow | slow | slow | normal |
| Colony | white, cushony wooly-flocky | white to cream, cushiony, wooly-flocky, back of the colony is colourless; | white, cushiony, wooly-flocky | white to cream cushony, wooly-flocky back of the colony of creamy-yellow; |
|  | size: NA | size: 15–20 mm | size: NA | size: 20–30 mm |
| Hyphae-size | 1–1.5–2 um | 1–1.5–3 um; cells 2.5–27 um long | 1–1.5–2 um | 2–6 um; cells 6–30 um long |
| Conidiophores | short with lateral or terminal dense whorls of phialids with bulbous bases | as in T. inflatum | as in T. inflatum | short, cylindrical with lateral and terminal whorls of phialids with bulbous bases. |
| Phialids Sterigma | NA filamentous | size: 3–5 × 2–2.8 um thin, filamentous sometimes bent size: 1.5–2 × 0.3–0.5 um | NA filamentous | size: 4–3 × 2–4 um thin, filamentous sometimes curved size: 2–4 × 0.6–1.2 um |
| Conidia | hyaline smooth unicellular | hyaline smooth, unicellular; single as well as stick together in groups of 20 and more, usually spherical sometimes adjacent parallels, cylindrical, sometimes slightly curved with rounded ends: size 4–5.8 × 1.2–1.6 um | hyaline smooth unicellular | hyaline smooth, unicellular, spherical to cylindrical, sometimes slightly curved with rounded ends. borne singly (2–4 × 1.2 um) as well as accumulate in slime heads (2–10 in numbers & 2–6 × 1–3 um in size) laterally and terminally. |

According to this invention there is provided a process for the preparation of cyclosporin A from Tolypocladium sp as herein described which comprises in subjecting said Tolypocladium sp to the step of fermentation in a nutrient medium to obtain a fermented medium extracting the fungal biomass of said fermented medium with methanol to obtain a methanol extract, removing methanol from said extract by the step of evaporation to obtain a first residue, preparing an aqueous solution of said first residue, preparing an ethyl acetate extract of said aqueous solution, decolourizing and concentrating said extract to obtain a second residue and then purifying the second residue chromatographically in two stages namely in a first stage on silica gel column as solid phase and a solvent mixture of hexane, chloroform and methanol as mobile phase and a second stage on resin column as solid phase and methanol as mobile phase.

The process details are discussed in FIG. 1 and FIGS. 2b–2b wherein two types of fermentation techniques namely (i) Static and (ii) solid substrate fermentaions are described.

In accordance with this invention, a small quantity of soil is made into a suspension in sterilized water and then diluted multifold with distilled water. A small portion of the diluted soil suspension is spread over a culture medium.

The culture medium is maintained at a pH of, for example 6.5 and consists of dextrose, peptone, Agar and water. Necessary amount of an agent such as streptomycin sulphate is added to the culture medium to prevent bacterial growth.

The soil suspension prepared above is then spread on the above solid surface of the culture medium, taken on a suitable container such as petri dish.

Incubation of the petri dishes is carried out at temperatures of around 22°–30° C. Substantial growth of fungal colonies are noticed after seven days. When the growth of fungal colony is considered satisfactory, the growth is terminated.

The individual fungal colonies are transferred to small quantitites of same culture medium held in test tubes which are sealed and stored at 25° C.

The remnants of the colonies are examined under microscope and identified to generic level. One of them had the characteristics of the fungus Tolypocladium and the findings have already been given in Table-1. This Tolypocladium species of the present invention was grown in a nutrient medium containing glucose, peptone, casein acid hydrolysate and sterile water maintained at a pH between 4–6, inoculating loopful of spore suspension of the species to agar slopes containing malt extract, yeast extract and agar at a pH of 4–6, incubating agar slopes till the culture attends the stage of operation.

When sufficient growth is achieved, the culture is transferred to glass ampoules and subjected to lyophilisation.

In the instance of obtaining cyclosporin A by solid-state fermentation, the master seed as obtained above is inoculated to a liquid medium. After sufficient growth the culture is transferred to solid substrate fermentation trays having sterilized wheat bran/rice bran and held at a pH of from 4 to 6. By maintaining a relative humidity of about 85 to 90% at temperature of 25° to 30° C., with aeration, growth of the fungus occurs on the solid substrate. Fungal growth along with the nutrient medium was extracted with methanol and was subjected to evaporation to obtain a first residue which was dissolved in sterile water to obtain an aqueous solution. An ethyl acetate extract of said aqueous solution is decolourized and concentrated to obtain a second residue. The second residue is subjected to two step column chromatography on a silica gel column for the first step and a resin column for the second step and wherein a solvent mixture of hexane, chloroform and methanol at the ratio 10:9:1 was employed as mobile phase for the first stage. For the second step of chromatography, methanol is used as mobile phase. Cyclosporin A of high purity is obtained in this two step chromatography.

In the instance of the static fermentation method the master seed is inoculated to a liquid medium in two stages to build up the inoculum of the species. The medium comprising glucose, peptone, casein acid hydrolysate and sterile water and incubated for 3–4 days is the first stage and 2–3 days is the second stage at 25° C. and transferring the inoculum so obtained to the static fermentation medium comprising gluclose, glycerol, casein acid hydrolysate, malt extract of peptone and DL-alpha amino butyric acid in sterile water at pH of 4–6 and allowing the fermentation for 21 days. The said medium comprises 2 to 6% of glucose, 2 to 5.5% of glycerol, 1.5 to 5.5% of casein acid hydrolysate, 0.5 to 4.5% of malt extract, 0.25 to 2.5% of peptone, 0.1 to 3% of DL alpha amino butyric acid and remainder sterile water.

By way of example, the medium contains 4% of glucose, 4% of glycerol, 3% of casein acid hydrolysate, 2% of malt extract, 1% of peptone, 0.5% of DL-alpha amino butyric acid.

The yield of cyclosporine A becomes substantially low if the ingredients are incorporated beyond the given range.

The biomass of the Tolypocladium fungus grown in the said static fermentation medium is filtered and the fungal biomass thus recovered is subjected to extraction in an organic solvent, such as methanol. Methanol is evaporated from the methanol extracted to obtain a first residue, the residue is dissolved in distilled water to obtain an aqueous solution, which is extracted with ethyl acetate to obtain an ethyl acetate extract. The extract is washed with sodium and evaporated to obtain a second residue and this residue is subjected to a two stage column chromatographic separation, as described hereinabove.

Both the steps of column chromatography provided a yield of cyclosporin A of 98% purity.

In FIG. 1, we have explained a typical process of preparation of cyclosporin A by using the step of static fermentation.

TABLE 2

Figure 1:
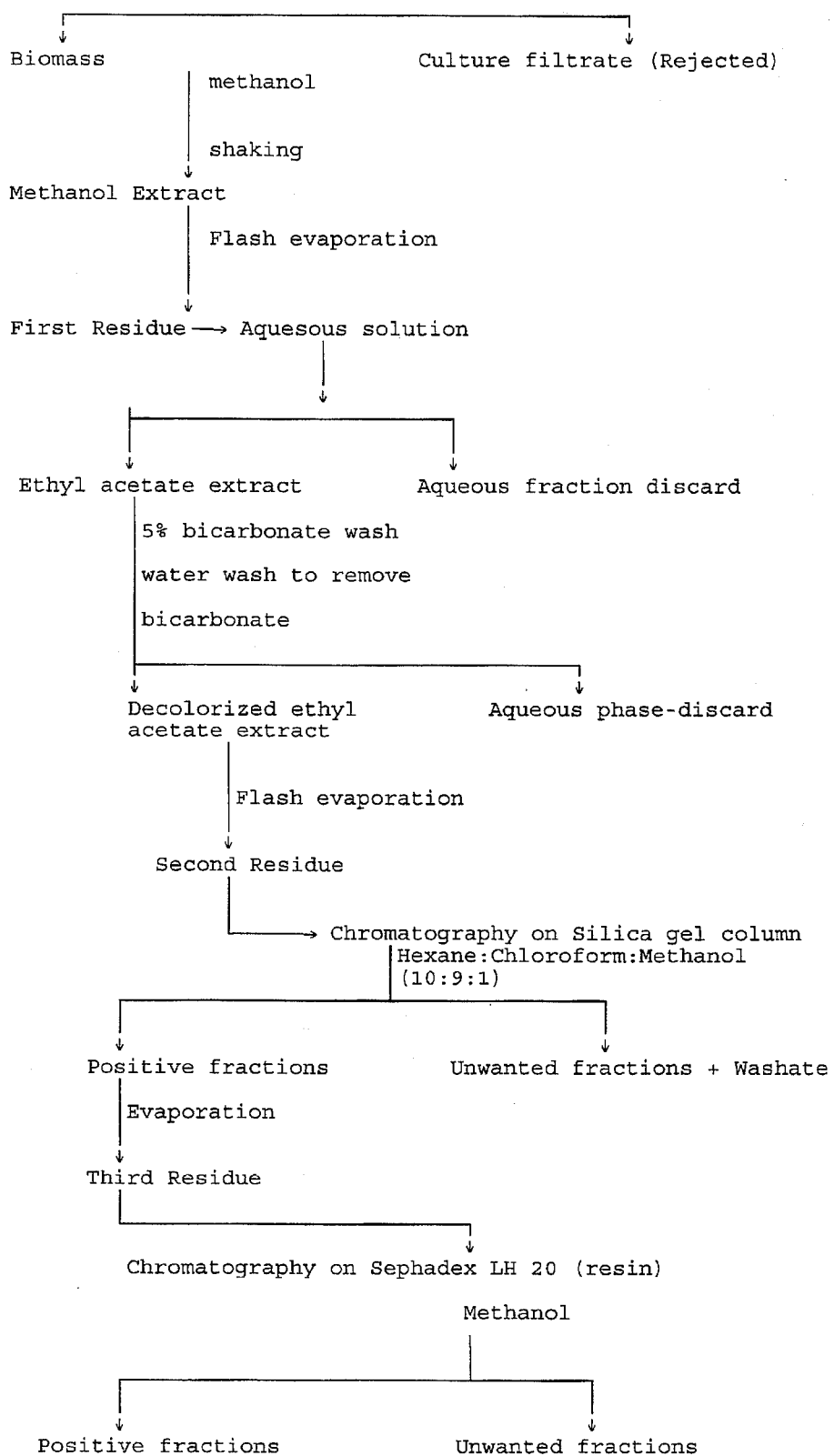
FIG. 1. Process of preparing cyclosporin A using static fermentation.
Figure 2A:
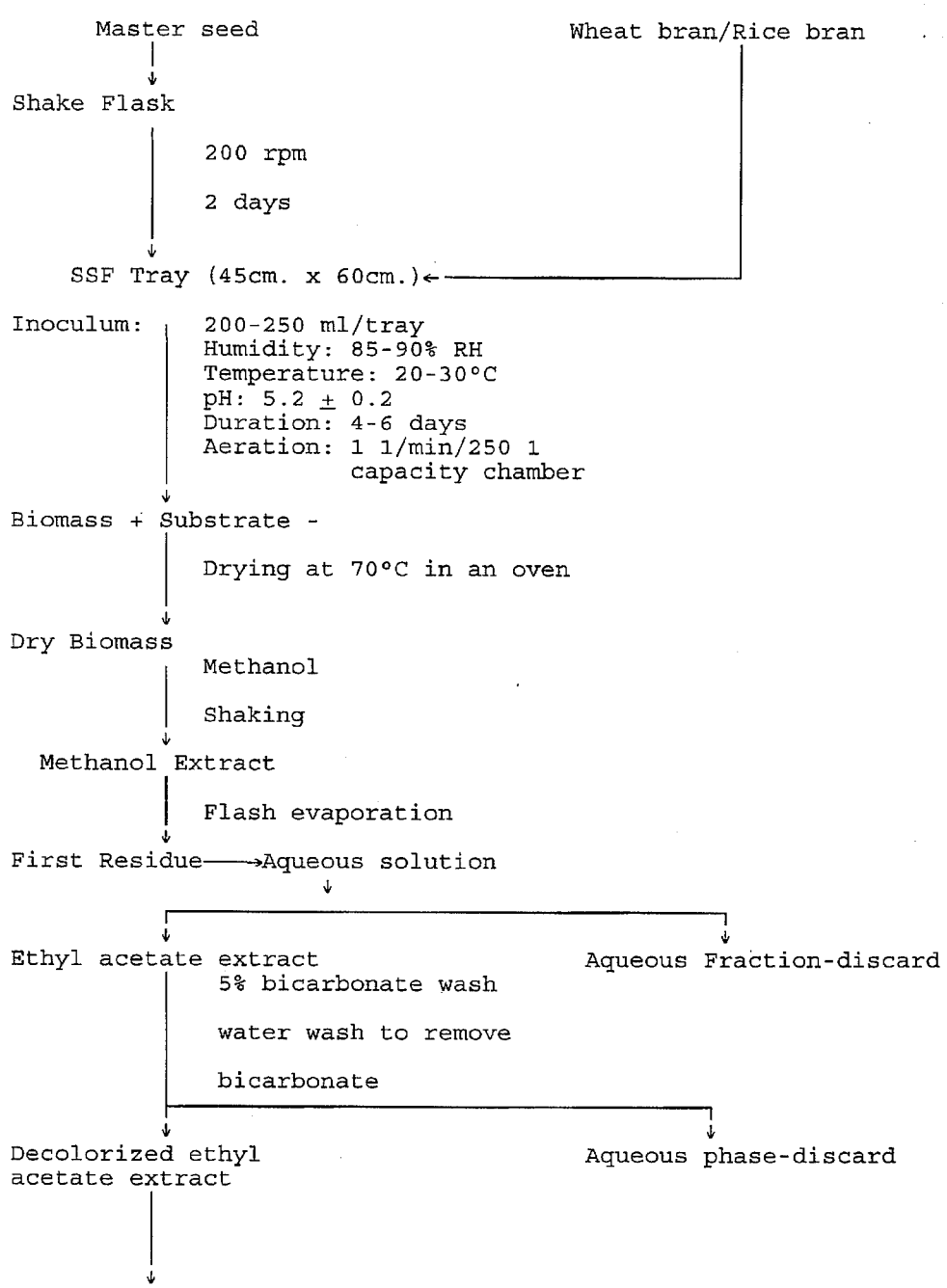
FIG. 2a–FIG. 2b. Process of preparing cyclosporin A using substrate fermentation.
Figure 2B:
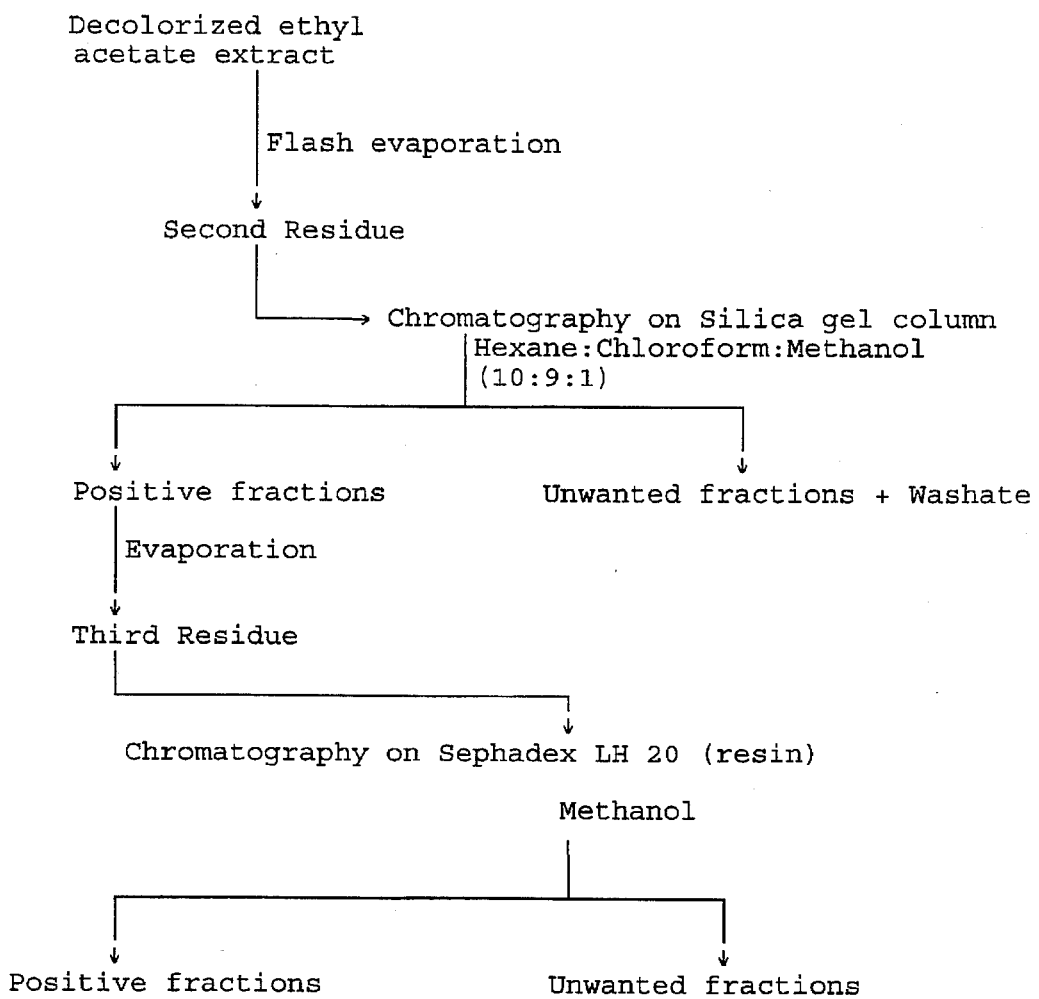

Yield of Cyclosporin A by the process of present invention by static fermentation.

| Experiment | Yield of cyclosporin A (mg/lit of medium) | | % Purity |
|---|---|---|---|
| | Crude form | Pure form | |
| 1. | 1519.6 | 1132.0 | 98.2 |
| 2. | 1798.0 | 1268.8 | 98.5 |
| 3. | 1889.0 | 1226.4 | 99.6 |
| 4. | 1749.8 | 1280.0 | 100.0 |
| 5. | 1801.4 | 1238.0 | 99.9 |
| 6. | 1887.0 | 1394.0 | 99.9 |
| Mean | 1774.1 | 1256.3 | 99.4 |

Source of isolation of different species of Tolypocladum and their cyclosporin yield

| Species | Source | Cyclosporin(mg/l) | Reference |
|---|---|---|---|
| Tolypocladium sp. | Soil/litter habitats, terrestrial invertebrates, myxomycete sporangia- | NA | Gams. Persoonia )1971)6:185–191 |
| *T. inflatum* UAMH Acc. No. | | | Isaac et al. |
| 2472 | water | 101 ± 61 | Antimicrob. Agents Chemother (1990) 34:121–127. |
| 2880 | Soil under *Pinus contorta* | 34 ± 41 | " |
| 4002 | muskec soil | 1223 ± 75 | " |
| 4553 | soil | 32 ± 27 | " |
| 4594 | washed organic particle from alpine meadow | 45 ± 38 | " |
| 4740 | soil | 12 ± 11 | " |
| 4828 | humus of alpine soil | 60 ± 35 | " |
| 4900 | mite surface (Mycobates sp.) | 15 ± 8 | " |
| 4901 | humified organic material | 24 ± 12 | " |
| Atcc 34921 | NA | 130 & 710 | Lee & Agathos, Appl. Microbiol, Biotechnol (1991) 34:513–517. |
| NRRL 8044 | NA | 101 | Von Wartburg & Traber Proc. Allercy (1986) 38:28–45. |
| *T. Cylindrosporum* | Larvae of Aedas mosquitoes | NA | Soares et.al. Proc. Pap. Annu. Conf. Calif. Mosq. Vector Control Assoc. (1979) 47:51–54 and Weiser and Pillai, Entomophaga (1981) 26:357–361 |
| Tolypocladium sp. of prsent invention by by static fermentation | soil of mosquito breeding habitat | 2000 ± 100 | unpublished data |

NA = Information not available

We claim:

1. A process for the preparation of cyclosporin A from Tolypocladium sp comprising subjecting said Tolypocladium sp to fermentation in a nutrient medium to obtain a fermented medium, extracting the fungal biomass of said fermented medium with methanol to obtain a methanol extract, removing methanol from said extract by evaporation to obtain a first residue, preparing an aqueous solution of said first residue, preparing an ethyl acetate extract of said aqueous solution, decolourizing and concentrating said extract to obtain a second residue and purifying the second residue chromatographically in a first stage on a silica gel column as solid phase with a solvent mixture of hexane, chloroform and methanol as mobile phase and a second stage on a resin column as solid phase and methanol as mobil phase.

2. A process as claimed in claim 1 wherein the fermentation is carried out by static fermentation.

3. A process as claimed in claim 1 wherein the fermentation is carried out by solid substrate fermentation.

4. A process as claimed in claim 1 wherein said Tolypocladium Sp inoculated into the nutrient medium is a master seed.

5. A process as claimed in claim 4, further comprising suspending spores of said Tolypocladium Sp in a medium containing glucose, peptone, casein acid, hydrolysate and sterile water maintained at a pH of between 4–6, inoculating a loopful of spore suspension of the species to agar slopes containing malt extract, yeast extract and agar at a pH of 4–6, and incubating said agar slopes until the culture attends the stage of sporulation to obtain the master seed.

6. A process as claimed in claim 1, which further comprises the step of building up of the inoculum of the species in at least a two stage process for inoculation into the fermentation medium.

7. A process as claimed in claim 6 wherein said first stage comprises transferring the master seed to a medium containing glucose, peptone, casein acid hydrolysate and sterile water at a pH of 4–6, and allowing growth for 3–4 days.

8. A process as claimed in claim 6 wherein said second stage comprises transferring the culture obtained from the first stage to a medium containing glucose, peptone, casein acid hydrolysate and sterile water at a pH of 4–6 and allowing growth for 2–3 days.

9. A process as claimed in claim 5, wherein the step of incubation is carried out for a period of 10–14 days.

10. A process as claimed in claim 1, wherein the nutrient medium comprises glucose, glycerol, casein acid hydrolysate, malt extract, peptone and DL α-amino butyric acid in sterile water at a pH of 4–6.

11. A process as claimed in claim 10 wherein said medium comprises 2 to 6% glucose, 2 to 5.5% glycerol, 1.5 to 5.5% casein acid hydrolysate, 0.5 to 4.5% malt extract, 0.25 to 2.5% peptone, 0.1 to 3% DL alpha amino burytic acid and sterile water.

12. A process as claimed in claim 1, wherein said step of decolourization is carried out by washing the ethyl acetate extract with sodium bicarbonate solution followed by water.

13. A process as claimed in claim 1, wherein the methanol extract of said biomass is prepared by shaking the biomass with methanol and subjecting the methanol extract so obtained to flash evaporation to obtain a pasty residue.

14. A process as claimed in claim 13, wherein the methanol residue is dissolved in distilled water to obtain an aqueous solution and then extracted with ethyl acetate to obtain an ethyl acetate fraction extract which is treated with sodium bicarbonate and washed with water.

15. A process as claimed in claim 14 wherein, concentration of the ethyl acetate fraction is obtained by flash evaporation.

16. A process as claimed in claim 1, wherein said solvent mixture is made of hexane, chloroform and methanol in the respective ratio of 10:9:1.

17. A process as claimed in claim 2, wherein the nutrient medium comprises glucose, glycerol, casein acid hydrolysate, malt extract, peptone and DL α-amino butyric acid in sterile water at a pH of 4–6.

18. A process as claimed in claim 17, wherein said medium comprises 2 to 6% of glucose, 2 to 5.5% of glycerol, 1.5 to 5.5% of casein acid hydrolysate, 0.5 to 4.5% of malt extract, 0.25 to 2.5% of peptone, 0.1 to 3% of DL alpha amino butyric acid and remainder sterile water.

* * * * *